United States Patent [19]

Inoi et al.

[11] Patent Number: 4,642,287

[45] Date of Patent: Feb. 10, 1987

[54] PROCESS FOR PRETREATING BIOMASSES IN ADVANCE OF THEIR ENZYMATIC TREATMENT

[75] Inventors: Takeshi Inoi, Yokohamashi; Toshiaki Akabane, Tokyo; Yasuhiro Kurokawa; Shingo Matsuoka, both of Yokohamashi, all of Japan

[73] Assignee: Shinnenryoyu Kaihatsugijutsu Kenkyukumiai, Tokyo, Japan

[21] Appl. No.: 596,937

[22] Filed: Apr. 5, 1984

[30] Foreign Application Priority Data

Apr. 14, 1983 [JP] Japan .................................. 58/65896
Apr. 14, 1983 [JP] Japan .................................. 58/65897

[51] Int. Cl.$^4$ ...................... C12P 19/14; C12P 19/02; B01J 3/00; C13K 1/02
[52] U.S. Cl. ..................................... 435/99; 435/105; 127/1; 127/37
[58] Field of Search .................... 435/99, 105; 127/37, 127/1

[56] References Cited

U.S. PATENT DOCUMENTS 2,801,955  8/1957  Rutenberg et al. .................. 127/37
4,281,063  7/1981  Tsao et al. .......................... 127/37
4,395,543  7/1983  Wang et al. ......................... 127/37

OTHER PUBLICATIONS

Japanese Patent Abstract; J57198095, 4-12-82.
Japanese Patent Abstract; J57198094, 4-12-82.

Primary Examiner—Christine M. Nucker
Assistant Examiner—Patricia L. DeSantis
Attorney, Agent, or Firm—Fred Philpitt

[57] ABSTRACT

An improved process for pretreating biomasses in advance of their enzymatic treatment is provided which process comprises subjecting a biomass together with an aqueous solution of an alkaline compound to kneading and reaction in a biaxial extruder, and which process has advantages that a continuous treatment in a very short time is possible, and the heat quantity required for the pretreatment is greatly reduced.

12 Claims, No Drawings

PROCESS FOR PRETREATING BIOMASSES IN ADVANCE OF THEIR ENZYMATIC TREATMENT

BACKGROUND OF THE INVENTION

1. Field of the Invention

This invention relates to a process for pretreating biomasses in advance of their enzymatic treatment. More particularly it relates to a process for pretreating biomasses in advance of their enzymatic treatment which comprises treating a mixture of a biomass with an aqueous solution of alkaline compounds by means of a biaxial extruder.

2. Description of the Prior Art

Since the oil crisis in the year 1974 i.e. the so-called primary oil shock, review of various substitute resources and technical development for utilizing the resources have been advanced in order to avoid excessive dependency on fossil resources. Among the resources, biomasses have been particularly noted as reproducible resources, and techniques for utilizing them have been studied. Cellulose as a main component of biomasses is enzymatically or chemically decomposed into glucose which is fermentatively converted into ethanol which is, in turn, used as liquid fuels or chemical raw materials. Enzymolysis process of cellulose has such advantages that the process can be carried out under milder conditions than those in chemical decomposition process, complicated apparatus is unnecessary, etc. but the process also has the following drawbacks: (1) raw material biomasses, as they are, are difficult to be subject to the action of cellulase enzyme; (2) the reaction is slow; (3) a considerable cost is needed for enzyme preparation and its recovery and reuse are difficult; etc. As for the pretreatment process of biomasses in advance of their enzymolysis, fine-grinding treatment, alkali-cooking treatment, etc. have so far been known, but these treatments are not practical so much since any of them needs a considerable cost and treating time. Among them, Japanese patent applications Sho 56-80,998/1981 and Sho 56-80,999/1981 (Japanese patent application laid-open Nos. Sho 57-198094/1982 and Sho 57-198095/1982) (hereinafter referred to as prior inventions) are directed to substantially a combination of fine-grinding treatment with alkali-cooking treatment, and the treating time is as short as e.g. 0.25 to 4.0 hours and the percentage enzymolysis of the pretreated materials is as superior as e.g. 86.1 to 96.4%. However, the pretreated materials of the prior inventions have been still insufficient in that even if the percentage enzymolysis is high, the treating time is long. Thus, the present inventors have made extensive research on the pretreatment process for decomposing biomasses by means of cellulase enzyme, and have succeeded in a continuous pretreatment of biomasses by means of a biaxial extruder.

SUMMARY OF THE INVENTION

The present invention resides in the folloiwng process (1) as a main aspect:

(1) A process for pretreating biomasses in advance of their enzymatic treatment, which comprises subjecting a biomass together with an aqueous solution of an alkaline compound to kneading and reaction in a biaxial extruder.

The above process (1) further has as a first aspect the following constitutions (2)~(7):

(2) A process for pretreating biomasses in advance of their enzymatic treatment, which comprises mixing a biomass with an aqueous solution of an alkaline compound and thereafter introducing the mixture into a biaxial extruder to subject it to kneading and reaction.

(3) A process according to the above process (2) wherein said biomass is a material obtained by cutting and grinding a biomass and having an average particle diameter of 15 mm or less.

(4) A process according to the above process (2) wherein the amount of said aqueous solution of an alkaline compound is in the range of 0.6 to 2 times by weight the amount of said biomass, and the proportion by weight of said compound to said biomass is in the range of 10 to 24%.

(5) A process according to the above process (2) wherein the treating temperature of said mixture in said biaxial extruder is in the range of 60° to 230° C.

(6) A process according to the above process (2) wherein said biomass is at least one member selected from the group consisting of bagasse, Siebold's beech, silver magnolia, Yezo spruce (Picea jezoensis CARR), white birch, corn rachis and used papers.

(7) A process according to the above process (2) wherein said alkaline compound is NaOH, $Na_2S$ or mixture thereof.

The above process (1) further has as a second aspect the following constitutions (8)~(13):

(8) A process for continuously pretreating biomasses in advance of their enzymatic treatment, which comprises introducing a biomass into a biaxial extruder and thereafter subjecting in to contact, kneading and reaction with an aqueous solution of an alkaline compound in the extruder.

(9) A process according to the above process (8) wherein said biomass is a material obtained by cutting and grinding a biomass and having an average particle diameter of 30 mm or less.

(10) A process according to the above process (8) wherein said aqueous solution of an alkaline compound in an amount of 3 to 15 times by weight the amount of said biomass is injected into said biaxial extruder, and the proportion by weight of said compound to said biomass is in the range of 3 to 30%.

(11) A process according to the above process (8) wherein the treating temperature in said biaxial extruder is in the range of 60° to 230° C.

(12) A process according to the above process (8) wherein said biomass is at least one member selected from the group consisting of bagasse, Siebold's beech, silver magnolia, Yezo spruce (Picea jezoensis CARR), white birch, corn rachis and used papers.

(13) A process according to the above process (8) wherein said alkaline compound is NaOH, $Na_2S$ or mixture thereof.

DETAILED DESCRIPTION OF THE PREFERRED EMBODIMENTS (i) Biomasses as a raw material of the present invention:

Any of cellulosic resources may be generally used therefor. However, since the present invention is directed to an efficient pretreatment process, the form and moisture of biomasses raise a problem. Whether the resources are arboreus plants or perbaceous plants, it is desirable that they have been cut or ground to an adequate dimension and the moisture contained therein has been adequately removed or adjusted. As to the form and moisture, in order to ease rapid permeation of the aqueous solution of an alkaline compound and washing-off of the treating solution, the length is made 15 mm or less, preferably 2 mm or less and the moisture is made 100% by weight or less, preferably 5 to 50% by weight based on their dry weight, in the case of the above process (2) as the first aspect. On the other hand, in the case of the above process (8) as the second aspect, the average particle diameter is made 30 mm or less, preferably 15 mm or less. As to the kinds of biomasses, any of cellulosic materials may be used such as arboreus materials e.g. Siebold's beech, silver magnolia, Yezo spruce (Picea jezoensis CARR), white birch, etc. or perbaceous materials e.g. bagasse, rice straw, wheat straw, corn rachis, etc. or cellulosic material e.g. used papers. Among them, bagasse which has already been ground and pressed up to a considerable extent when produced, is one of desirable raw materials.

(ii) The aqueous solution of an alkaline compound used in the present invention:

In the above process (2) as the first aspect, the solution is used in an amount of 0.6 to 2 times by weight the amount of the biomass. If the amount of the solution is less than 0.6 times by weight, rapid and uniform agitation and permeation are difficult. On the other hand, even if it exceeds twice by weight, there is no particular improvement in effectiveness. Such an excess amount is rather undesirable since the heating effect is reduced, the quantity of energy required is increased, and the moisture is squeezed out in an excess amount exceeding a certain extent by the screw and cylinder of the extruder so that the amount of the solution collects in the vicinity of the biomass-introducing port of the extruder to hinder a long time operation. In the above process (10) as the second aspect, the aqueous solution of an alkaline compound is used in an amount of 3 to 15 times the amount of biomass. If the amount is less than 3 times by weight, rapid and uniform mixing and permeation are difficult, while even if it exceeds 15 times by weight, there is no particular improvement in effectiveness. As the alkaline compound, NaOH, $Na_2S$ or mixture thereof is used in an amount of 10 to 24% by weight based on the amount of biomass in the case of the above process (2) as the first aspect. On the other hand, in the case of the above process (10) as the second aspect, it is used in an amount of 3 to 30% by weight. If the proportion is lower than those in the above ranges, the pretreatment effectiveness of the present invention is reduced, while even if it exceeds the above ranges, there is no particular effectiveness. As the compound used, any of NaOH, $Na_2S$ and mixture thereof is effective, and the proportion of the mixture may be optional, but the proportion by weight of NaOH/$Na_2S$ is preferred to be in the range of 1 to 5 times.

(iii) Pretreatment conditions:

The biomasses of the above item (i) and the aqueous solution of an alkaline compound, both used in the above process (2) as the first aspect, are in advance mixed with stirring and then introduced into an extruder. As this feeder, a biaxial screw feeder may be used which has usually been used for extruding plastic pellets or powder.

The biomasses of the above item (i) used in the above process (8) as the second aspect are introduced into an extruder, and an aqueous solution of an alkaline compound is injected through a feeding port or a vent port separately provided at a biomass-feeding port, and they are kneaded and reacted. For the introduction, a biaxial screw feeder may be used which has usually been used for plastic pellets or powder.

A biaxial extruder is used for the extruder. Monoaxial extruders are unsuitable for pretreating biomasses since they are insufficient in kneading and extruding performances.

The revolving direction of the screw may be either in the same or different directions. The treating temperature (the cylinder temperature of the extruder) is in the range of 60° to 230° C., preferably 90° to 230° C. The retention time of the biomass mixed with the aqueous solution of an alkaline compound with stirring, within the biaxial extruder, i.e. the pretreating time, is one minute or shorter.

(iv) Characteristic effectiveness of the present invention:

As apparent from the foregoing description, the effectiveness of the present invention is as follows:

It is possible to carry out a continuous treatment in a very short pretreating time. Further, particularly in the case of the above process (2) as the first aspect, the liquid ratio is low; hence it is also possible to reduce the heat quantity required for heating down to a large extent. Further, in the case of the above process (8) as the second aspect, when the biomass is introduced into the extruder, it has not yet been mixed with the aqueous solution of an alkaline compound; hence it is easy to introduce the biomass.

Whereas, in the past pretreatment processes (excluding the prior inventions), for example, fine-grinding treatment requires times as long as several hours to several tens hours, and for example, alkali treatment requires cooking times as long as several tens minutes to several hours in order to obtain a percentage enzymolysis of 50% or higher. Further, cooking requires the aqueous solution of an alkaline compound in an amount of 5 to 20 times by weight the amount of biomass; hence the heat quantity required for heating water becomes very large.

The present invention will be further described in detail by way of Examples.

Various tests in Examples were carried out as follows:

(1) Percentage Enzymolysis and Percentage Enzymatic Saccharification

To a sample (1%) and an enzyme (1%) was added a 0.1M-acetic acid buffer so as to give a volume of 10 ml. Using a L-letter test tube (18 mm$\phi$, 100 mm high × 120 mm long), mono-shaking (46 reciprocations/min.) was carried out at 50° C. for 4 hours. As the enzyme, Cellulase Onozuka R-10 (Trichoderma Viride Cellulase made by Yakuruto Biochemicals) was used. After the reaction, the enzymatic reaction liquor was filtered through a glass fiber filter paper (Toyo filter paper GC-50) and the filtration residue was washed with water, followed by drying at 105° C. overnight and weighing. The percentage enzymolysis was calculated from the following equation:

Percentage enzymolysis (%) =

$$\left(1 - \frac{\text{Filtration residue}}{\text{Sample (dry)}}\right) \times 100$$

Further, glucose in the filtrate was measured and the percentage enzymatic saccharification was calculated from the following equation:

Percentage enzymatic saccharification =

$$\frac{\text{Glucose formed} \times 0.9}{\text{Sample (dry)}} \times 100$$

(2) Lignin Content

This content was sought by a testing method for lignin in pulp materials according to JIS P8008 (1976).

EXAMPLES 1~8

To bagasse ground to an average particle diameter of 15 mm or less was added an aqueous solution containing NaOH in an amount of 20% by weight based on the bagasse, in definite amounts shown in Table 1, followed by mixing with stirring. The mixture of bagasse was introduced into a biaxial extruder and treatment was carried out at a cylinder temperature of the extruder of 200° C. After the treatment, the bagasse was washed with water and then with acetone and air-dried. The lignin content and the percentage enzymolysis were measured according to the above definite testing methods.

The results are shown in Table 1. As seen from this Table, the values of the lignin content and the percentage enzymolysis are both inferior to those of the prior inventions, but the values of the percentage enzymatic saccharification as a finally decisive factor are to the same extent to that of the prior inventions. On the other hand, the treating time of the prior inventions is 15 minutes or longer, whereas that of the present invention is as extremely short as one minute or less.

TABLE 1

| | NaOH*[1] (%) | Liquid ratio*[2] | Particle diameter of sample (mm or less) | Treating temperature (°C.) | Lignin content (%) | Percentage enzymolysis (%) | Percentage saccharification (%) |
|---|---|---|---|---|---|---|---|
| Example 1 | 20 | 0.6 | 215 | 200 | 11.2 | 67.0 | 34.7 |
| Example 2 | " | 0.8 | " | " | 9.0 | 80.8 | 49.8 |
| Example 3 | " | 1.0 | " | " | 9.3 | 84.8 | 47.1 |
| Example 4 | " | 1.2 | " | " | 10.3 | 73.6 | 48.1 |
| Example 5 | " | 1.4 | " | " | 10.1 | 74.5 | 46.6 |
| Example 6 | " | 1.6 | " | " | 10.5 | 75.5 | 51.1 |
| Example 7 | " | 1.8 | " | " | 10.3 | 72.3 | 47.0 |
| Example 8 | " | 2.0 | " | " | 9.5 | 78.5 | 43.5 |

Note:
*[1] Based on absolutely dried bagasse (this applies to the succeeding Tables).
*[2] Number of times by weight of the aqueous solution of an alkaline compound, based on the weight of absolutely dried bagasse (this applies to the succeeding Tables).

EXAMPLES 9~16

Examples 1~8 were repeated except that the alkaline compound was replaced by a mixture of $Na_2S$ with NaOH. The results are shown in Table 2.

TABLE 2

| | $Na_2S \cdot NaOH$* (%) | Liquid ratio | Lignin content (%) | Percentage enzymolysis (%) | Percentage Saccharification (%) |
|---|---|---|---|---|---|
| Example 9 | 20 | 0.6 | 10.9 | 78.7 | 48.3 |
| Example 10 | " | 0.8 | 10.7 | 82.2 | 45.0 |
| Example 11 | " | 1.0 | 10.7 | 83.9 | 38.9 |
| Example 12 | " | 1.2 | 9.6 | 86.6 | 48.2 |
| Example 13 | " | 1.4 | 9.8 | 82.7 | 50.7 |
| Example 14 | " | 1.6 | 8.7 | 86.1 | 50.2 |
| Example 15 | " | 1.8 | 7.8 | 87.4 | 48.0 |
| Example 16 | " | 2.0 | 6.6 | 88.3 | 49.8 |

Note:
*$Na_2S:NaOH = 3:7$

EXAMPLES 17~19

Example 3 was repeated except that the amount of NaOH was varied. The results are shown in Table 3.

TABLE 3

| | NaOH (%) | Liquid ratio | Lignin content (%) | Percentage enzymolysis (%) | Percentage saccharification (%) |
|---|---|---|---|---|---|
| Example 17 | 16 | 1.0 | 14.3 | 67.0 | 31.5 |
| Example 18 | 18 | " | 10.5 | 81.5 | 39.6 |
| Example 19 | 20 | " | 9.2 | 85.9 | 53.8 |

EXAMPLES 20~24

Example 11 was repeated except that the amount of the mixture of $Na_2S \cdot NaOH$ was varied. The results are shown in Table 4.

TABLE 4

| | $Na_2S \cdot NaOH$ (%) | Liquid ratio | Lignin content (%) | Percentage enzymolysis (%) | Percentage saccharification (%) |
|---|---|---|---|---|---|
| Example 20 | 12 | 1.0 | 13.4 | 67.8 | 35.1 |
| Example 21 | 14 | " | 10.5 | 79.9 | 41.8 |
| Example 22 | 16 | " | 8.5 | 85.5 | 49.5 |
| Example 23 | 18 | " | 7.5 | 85.7 | 55.2 |

TABLE 4-continued

| | Na₂S·NaOH (%) | Liquid ratio | Lignin content (%) | Percentage enzymolysis (%) | Percentage saccharification (%) |
|---|---|---|---|---|---|
| Example 24 | 20 | " | 6.0 | 89.2 | 55.6 |

EXAMPLES 25~28

Examples 17~20 were repeated except that the reagent was replaced by Na₂S. The results are shown in Table 5.

TABLE 5

| | Na₂S (%) | Liquid ratio | Lignin content (%) | Percentage enzymolysis (%) | Percentage saccharification (%) |
|---|---|---|---|---|---|
| Example 25 | 14 | 1.0 | 12.2 | 72.3 | 35.6 |
| Example 26 | 16 | " | 11.2 | 78.2 | 38.2 |
| Example 27 | 18 | " | 9.6 | 78.8 | 45.6 |
| Example 28 | 20 | " | 8.2 | 83.0 | 54.2 |

EXAMPLES 29~34

Example 26 was repeated except that the treating temperature was replaced by 60°~210° C. The results are shown in Table 6.

TABLE 6

| | Na₂S·NaOH (%) | Liquid ratio | Treating temperature (°C.) | Lignin content (%) | Percentage enzymolysis (%) | Percentage saccharification (%) |
|---|---|---|---|---|---|---|
| Example 29 | 20 | 1.0 | 60 | 14.4 | 61.2 | 35.0 |
| Example 30 | " | " | 90 | 12.0 | 72.7 | 43.5 |
| Example 31 | " | " | 120 | 11.0 | 73.1 | 47.7 |
| Example 32 | " | " | 150 | 10.9 | 85.7 | 44.0 |
| Example 33 | " | " | 180 | 7.6 | 86.9 | 49.8 |
| Example 34 | " | " | 210 | 7.6 | 87.8 | 51.6 |

EXAMPLES 35~40

Treatments were carried out wherein the particle diameter of sample was varied. The results are shown in Table 7.

TABLE 7

| | Particle diameter of sample | Amount of reagent (%) NaOH | Amount of reagent (%) Na₂S | Liquid ratio | Treating temperature (°C.) | Lignin content (%) | Percentage enzymolysis (%) | Percentage saccharification (%) |
|---|---|---|---|---|---|---|---|---|
| Example 35 | 0.17~0.35 | 18 | 0 | 1.0 | 200 | 11.4 | 77.9 | 44.8 |
| Example 36 | " | 12.6 | 5.4 | " | " | 7.3 | 88.3 | 60.0 |
| Example 37 | 2 mm or less | 18.0 | 0 | " | " | 10.5 | 81.5 | 39.6 |
| Example 38 | | 12.6 | 5.4 | " | " | 7.5 | 85.7 | 55.2 |
| Example 39 | 15 mm or less | 18.0 | 0 | " | " | 10.3 | 82.9 | 42.6 |
| Example 40 | | 12.6 | 5.4 | " | " | 9.5 | 84.3 | 49.6 |

EXAMPLES 41~44

Treatments were carried out wherein samples obtained by grinding and sieving Siebold's beech, silver magnolia, Yezo spruce and corn rachis to 2 mm or less were used. The results are shown in Table 8.

TABLE 8

| | Kind | Na₂S·NaOH* (%) | Liquid ratio | Particle diameter of sample | Treating temperature (°C.) | Lignin content (%) | Percentage enzymolysis (%) | Percentage saccharification (%) |
|---|---|---|---|---|---|---|---|---|
| Example 41 | Siebold's beech | 20 | 1.0 | 2 mm or less | 200 | 10.2 | 68.2 | 38.2 |
| Example 42 | Silver magnolia | " | " | 2 mm or less | " | 8.9 | 70.3 | 40.5 |
| Example 43 | Yezo spruce | " | " | 2 mm or less | " | 10.5 | 58.6 | 32.6 |
| Example 44 | Corn rachis | 15 | " | 2 mm or less | " | 7.3 | 85.3 | 54.2 |

Note:
*Na₂S:NaOH = 3:7

EXAMPLES 45~50

Bagasse ground to a length of 30 mm or less was introduced and a 4% aqueous solution of the mixture of Na₂S·NaOH was injected through a vent port, followed by kneading and reaction. Treatment was carried out at a cylinder temperature of extruder of 200° C. After the treatment, the bagasse was filtered, washed with water and further with acetone and air-dried. The lignin content and the percentage enzymolysis of the thus treated bagasse were measured according to the definite testing methods. The results are shown in Table 9.

TABLE 9

| | Na₂S.NaOH* (%) | Flow amount of reagent (l/hr) | Particle diameter of sample (mm or less) | Amount of sample fed (kg/hr) | Treating temperature (°C.) | Lignin content (%) | Percentage enzymolysis (%) | Percentage saccharification (%) |
|---|---|---|---|---|---|---|---|---|
| Example 45 | 4 | 16.8 | 30 | 5.2 | 200 | 7.5 | 83.8 | 43.3 |
| Example 46 | " | 27.0 | " | " | " | 7.1 | 73.3 | 52.1 |
| Example 47 | " | 37.2 | " | " | " | 6.0 | 70.5 | 53.8 |
| Example 48 | " | 47.4 | " | " | " | 6.2 | 72.5 | 58.1 |
| Example 49 | " | 57.6 | " | " | " | 6.4 | 70.7 | 53.8 |
| Example 50 | " | 67.8 | " | " | " | 7.2 | 63.8 | 49.1 |

Note:
*Na₂S:NaOH = 3:7

The present invention is different from the prior inventions in cooking conditions; hence a simple comparison between them is impossible. The former is somewhat inferior to the latter in both the lignin content and the percentage enzymolysis. However, the percentage enzymatic saccharification as a finally decisive factor, of the present invention is to the same extent as those of the prior inventions. On the other hand, the treating time of the present invention is as extremely short as one minute or less, whereas those of the prior inventions are 15 minutes or longer.

EXAMPLES 51~56

Example 3 was repeated except that the concentration of the mixture of Na₂S·NaOH was varied. The results are shown in Table 10.

TABLE 10

| | Concentration of reagent (%) | Lignin content (%) | Percentage enzymolysis (%) | Percentage saccharification (%) |
|---|---|---|---|---|
| Example 51 | *Na₂S.NaOH 1 | 8.3 | 68.7 | 37.2 |
| Example 52 | *Na₂S.NaOH 2 | 7.6 | 73.6 | 49.8 |
| Example 53 | *Na₂S.NaOH 4 | 6.0 | 70.0 | 53.8 |
| Example 54 | *Na₂S.NaOH 10 | 8.5 | 63.6 | 47.8 |
| Example 55 | NaOH 4 | 8.2 | 68.2 | 42.3 |
| Example 56 | Na₂S 4 | 8.0 | 70.5 | 50.5 |

Note:
*Na₂S.NaOH = 3:7

EXAMPLES 57~59

Example 47 was repeated except that the particle diameter of sample was varied. The results are shown in Table 11.

TABLE 11

| | Na₂S.NaOH* (%) | Particle diameter of sample (mm or less) | Lignin content (%) | Percentage enzymolysis (%) | Percentage saccharification (%) |
|---|---|---|---|---|---|
| Example 57 | 4 | 30 | 7.4 | 82.8 | 55.7 |
| Example 58 | " | 15 | 7.3 | 82.4 | 56.8 |
| Example 59 | " | 2 | 7.2 | 80.1 | 52.3 |

Note:
*Na₂S:NaOH = 3:7

EXAMPLES 60~64

Example 45 was repeated except that the temperature was varied. The results are shown in Table 12.

TABLE 12

| | Na₂S.NaOH (%) | Treating temperature (°C.) | Lignin content (%) | Percentage enzylmolysis (%) | Percentage saccharification (%) |
|---|---|---|---|---|---|
| Example 60 | 4 | 60 | 9.2 | 70.2 | 37.2 |
| Example 61 | " | 100 | 8.5 | 77.0 | 44.3 |
| Example 62 | " | 150 | 8.0 | 79.3 | 48.9 |
| Example 63 | " | 200 | 7.1 | 81.6 | 52.3 |
| Example 64 | " | 230 | 7.2 | 80.2 | 51.5 |

EXAMPLES 65~68

Treatments were carried out with samples obtained by grinding and sieving Siebold's beech, silver magnolia, Yezo spruce and corn rachis to 15 mm or less. The results are shown in Table 13.

TABLE 13

| | Kind | Na₂S.NaOH (%) | Flow amount of reagent (l/hr) | Amount of sample fed (Kg/hr) | Treating temperature (°C.) | Lignin content (%) | Percentage enzymolysis (%) | Percentage saccharification (%) |
|---|---|---|---|---|---|---|---|---|
| Example 65 | Siebold's beech | 4 | 37.2 | 5.2 | 200 | 9.5 | 63.8 | 33.6 |
| Example 66 | Silver magnolia | " | " | " | " | 9.8 | 68.2 | 35.2 |
| Example 67 | Yezo spruce | " | " | " | " | 9.8 | 54.5 | 32.3 |
| Example 68 | Corn rachis | " | 27.0 | 4.8 | " | 7.2 | 83.2 | 53.4 |

What we claim is:

1. In the process of pretreating a biomass in advance of cellulose enzymatic treatment that includes contacting the biomass in finely divided form with an aqueous solution of an alkaline compound, the improvement comprising reducing the pretreatment time to one minute or less by introducing the biomass and the alkaline compound into a biaxial extruder and carrying out the pretreatment in said biaxial extruder.

2. A process according to claim 1 wherein said alkaline compound is NaOH or $Na_2S$ or a mixture of NaOH and $Na_2S$.

3. A process according to claim 2 wherein said biomass and said aqueous solution of an alkaline compound are mixed together before being introduced into said biaxial extruder.

4. A process according to claim 3 wherein said biomass is a material obtained by cutting and grinding a biomass and has an average particle diameter of 15 mm or less.

5. A process according to claim 3 wherein the amount of said aqueous solution of an alkaline compound is in the range of 0.6 to 2 times by weight the amount of said biomass, and the alkaline compound is 10 to 24% by weight of said biomass.

6. A process according to claim 3 wherein the temperature of said mixture in said biaxial extruder is in the range of 60° to 230° C.

7. A process according to claim 3 wherein said biomass is at least one member selected from the group consisting of bagasse, Siebold's beech, silver magnolia, Yezo spruce (Picea jezoensis CARR), white birch, corn rachis and paper.

8. A process according to claim 2 wherein said biomass and said aqueous solution of an alkali compound are separately introduced into said biaxial extruder so that mixing thereof only occurs in the biaxial extruder.

9. A process according to claim 8 wherein said biomass is a material obtained by cutting and grinding a biomass and has an average particle diameter of 30 mm or less.

10. A process according to claim 8 wherein said aqueous solution of an alkaline compound, in an amount of 3 to 15 times by weight the amount of said biomass is injected into said biaxial extruder separately from the introduction of the biomass into the extruder and said alkaline compound is 3–30% by weight of said biomass.

11. A process according to claim 8 wherein the temperature in said biaxial extruder is in the range of 60° to 230° C.

12. A process according to claim 8 wherein said biomass is at least one member selected from the group consisting of bagasse, Siebold's beech, silver magnolia, Yezo spruce (Picea jezoenis CARR), white birch, corn rachis and papers.

* * * * *